United States Patent [19]

Telford

[11] 4,304,686

[45] Dec. 8, 1981

[54] METHOD OF PREPARING IMPROVED CATALYSTS

[75] Inventor: Clive D. Telford, Asford, England

[73] Assignee: The British Petroleum Company Limited, London, England

[21] Appl. No.: 182,309

[22] Filed: Aug. 28, 1980

[30] Foreign Application Priority Data

Sep. 4, 1979 [GB] United Kingdom .................. 30679/79

[51] Int. Cl.³ .......................... B01J 23/08; B01J 29/06
[52] U.S. Cl. ................................................. 252/455 Z
[58] Field of Search ..................... 252/455 Z; 423/112, 423/328

[56] References Cited

U.S. PATENT DOCUMENTS

| | | | |
|---|---|---|---|
| 3,253,887 | 5/1966 | Mattox et al. .................. | 252/455 Z |
| 3,367,884 | 2/1968 | Reid, Jr. ........................ | 252/455 Z |
| 3,431,219 | 3/1969 | Argawer ....................... | 252/455 Z |
| 4,150,062 | 4/1979 | Garwood et al. ............. | 208/DIG. 2 |
| 4,175,057 | 11/1979 | Davies et al. .................. | 252/455 Z |

*Primary Examiner*—Carl F. Dees

*Attorney, Agent, or Firm*—Brooks, Haidt, Haffner & Delahunty

[57] ABSTRACT

This invention relates to an improved method of preparing a zeolite composition in which some or all of the cations have been exchanged for gallium ions. The zeolite has a high silica to alumina ratio and is prepared by crystallization from an aqueous solution containing a mixture of a source of silica, a source of alumina, and at least two other components selected from the group of alkali metal ions, amonia and an organic nitrogen containing base. The improvement lies in washing the crystallized zeolite with acidified and/or deionized water, calcining the washed product at an elevated temperature, contacting the calcined product with an acid, refluxing the acid treated zeolite with a solution of a gallium compound to produce a gallium exchange zeolite and washing the gallium exchanged zeolite with water to render it substantially free from any impregnated gallium or gallium compound. The zeolite composition is useful as a catalyst for hydrocarbon conversion reactions.

10 Claims, No Drawings

METHOD OF PREPARING IMPROVED CATALYSTS

The present invention relates to a method of preparing active ion-exchanged zeolite catalysts.

Catalyst compositions based on crystalline aluminosilicates, i.e. zeolites, having a high silica to alumina ratio, particularly crystalline aluminosilicates prepared using organic nitrogen cations, are known. Catalyst compositions of this type comprising a zeolite which has been exchanged with a metal such as gallium are described for example in our European patent application Nos. 78300773.5 and 78300774.3, and Belgian Pat. No. 862051.

It has now been found that the activity of such catalyst compositions may be improved by subjecting the zeolites to a series of pretreatments prior to exchange with gallium.

Accordingly, the present invention is an improved method of preparing a catalyst composition comprising a zeolite in which some or all of the cations have been exchanged for gallium ions, said zeolite having a high silica to alumina ratio and being prepared by crystallisation from an aqueous solution comprising a mixture of a source of silica, a source of alumina, and at least two other components selected from the group of alkali metal ions, ammonia and an organic nitrogen containing base, said improvement comprising washing the crystallied zeolite with acidified and/or deionised water, calcining the washed product at an elevated temperature, contacting the calcined product with an acid, refluxing the acid-treated product with a solution of a gallium compound to produce a gallium exchanged zeolite and washing the gallium exchanged zeolite with water to render it substantially free from any impregnated gallium or gallium compound.

The zeolites having a high silica to alumina ratio are well known in the art. These are generally prepared by reacting in aqueous solution a mixture of a source of silica, a source of alumina, a source of alkali metal and an organic nitrogen containing base in appropriate proportions. This preparation may be modified by using ammonia instead of the alkali metal ions or the organic nitrogen containing base. The zeolite is allowed to crystallise from the solution by maintaining the solution at an elevated temperature under autogenous pressure.

Suitable sources of silica include, for example, sodium silicate, silica hydrosol, silica gel, silica sol, and silicic acid. The preferred source of silica is an aqueous colloidal dispersion of silica particles. A suitable commercially available source of silica is LUDOX Colloidal Silica manufactured by Du Pont (LUDOX is a Registered Trade Mark).

Suitable sources of alumina include, for example, sodium aluminate, aluminium sulphate and alumina. The preferred source of alumina is sodium aluminate prepared by dissolving alumina particles in excess sodium hydroxide solution.

Suitable sources of alkali metal include alkali metal hydroxides and alkali metal oxides. Preferably the alkali metal is sodium.

It will be appreciated that each source of silica, alumina and alkali metal can be supplied by one or more initial reactants and then mixed together in any order. For example sodium silicate is a source of both sodium and silica.

Where ammonia is used, this is converted to ammonium ions in the presence of water.

The organic nitrogen-containing base may be a quaternary ammonium base, for example a tetraalkylammonium compound derived from an alkylamine containing from 2 to 5 carbon atoms, e.g. propylamine. The organic nitrogen-containing base may also be pyrrolidine or an alkyldiamine containing from 2 to 20 carbon atoms, e.g. a pentanediamine or a hexanediamine. Preferably the organic nitrogen-containing base is an alkanolamine which may be a mono- or di-alkanolamine such as mono-ethanolamine, di-ethanolamine, mono-propanolamine or di-propanolamine, or a tri-alkanolamine as described in European patent application Nos. 78300773.5 and 78300774.3. The use of di-ethanolamine is particularly preferred.

The reaction conditions which effect the formation of the aluminosilicate may be, for example, a temperature in the range from 80° to 210° C., preferably from 100° to 190° C. The mixture may be held under these conditions for a time not less than 4 hours, preferably from 2 to 15 days.

The source of silica, alumina, water and any two of alkali metal ions, ammonia and nitrogen-containing base may be mixed in quite wide proportions. Thus the ratio of the silica source to the alumina source may be in the range from 10:1 to 500:1, preferably from 20:1 to 100:1 based on the equivalent moles of silica and alumina in the respective sources. The alkali metal source or ammonia may be present in an amount from 0.01 to 50, preferably from 0.04 to 2 moles of alkali metal or ammonia per mole equivalent of total silica and alumina in the respective sources. The organic nitrogen-containing base may suitably be present in an amount from 0.02 to 50, preferably from 0.1 to 10 moles per mole equivalent of total silica and alumina in their respective sources. The amount of water present is preferably between 100 and 2000 moles/mole of alumina.

The reaction is suitably carried out in a closed vessel capable of withstanding the elevated pressures generally employed during the process. Furthermore the reaction mixture may be agitated during the formation of the aluminosilicate.

The crystalline zeolite is suitably separated from the mother liquor by decantation. The crystals are then washed thoroughly with acidified and/or deionised water and the washed product is dired, for example by heating in air at temperature up to 120° C. The dried zeolite is then calcined at a temperature of at least 300° C., suitably between 300° and 800° C. for at least 6 hours, preferably 10 to 80 hours. The calcined zeolite is then treated with an acid. The acid treatment may be carried out by refluxing the zeolite with a mineral acid, preferably dilute nitric, acid, sulphuric acid, hydrochloric acid or hydrofluoric acid for a period of 0.5–24 hours. The acid treated product may be washed with water to remove any adherent acid and it is then dried as previously described.

The crystallised zeolite may be optionally subjected to one or more treatments with ammonia before or after acid treatment. This may be carried out by contacting the zeolite with ammonia in the gas phase or a solution of ammonia or an ammonium salt, e.g. ammonium nitrate, and then by washing with deionised water and drying as before to give an ammonia exchanged zeolite.

Where the acid treated zeolite is subjected to an ammonia exchange it has to be recalcined at elevated temperature, suitably between 350° and 700° C. for several hours.

The acid treated zeolite or the recalcined product after ammonia exchange is then subjected to a gallium exchange step. This step may be carried out by refluxing the zeolite product from the preceding stage with a solution of a gallium compound, e.g. gallium nitrate. The solution of the gallium compound may optionally contain in addition ammonium ions to control the pH of the solution. The gallium exchanged zeolite is thereafter washed with water to render it substantially free from any impregnated gallium or gallium compound. The water-washed gallium-exchanged zeolite is thereafter dried as previously described.

The gallium exchanged zeolites produced according to the process of the present invention exhibit a high degree of activity in hydrocarbon conversion reactions. For example these gallium-exchanged zeolites may be used as catalysts in the dehydrocyclodimerisation reactions claimed and described in our British Pat. Nos. 1,507,549 and 1,507,778 and in our Belgian Pat. No.: 862,051. In using these zeolites for such reactions it is preferable to pelletise or extrude these zeolites together with a base or binder. Such binders will be known to those skilled in the art. Examples of such binders include silica and alumina. Where silica is used e.g. in the form of a commercially available silica sol such as LUDOX (Registered Trade Mark) it may be added to the gallium-exchanged zeolite to form a slurry. The slurry thus formed may be extruded and dried to produce a material sufficiently strong to resist crushing.

The present invention is further illustrated with reference to the accompanying Examples.

EXAMPLE 1

(a) Zeolite Synthesis

In the synthesis of the zeolite the following reactants were used:

| | |
|---|---|
| Sodium hydroxide | 10.0 g |
| Sodium aluminate | 28.0 g |
| Diethanolamine | 262 g |
| Ludox AS 40 (Registered Trade Mark) | 714 g (40% w/w colloidal silica) |
| Deionized water | 850 g |

Sodium hydroxide and sodium aluminate were dissolved in deionised water (350 g) by warming and stirring for 10 minutes. The solution was then filtered and placed in a 3-liter flask. Diethanolamine was melted and added to this solution and the whole stirred for 10 minutes maintaining the temperature at 40° C. The colloidal silica was then diluted with the remainder of the deionised water (500 g) and then slowly added to the mixture in the flask, over a period of 1 hour. During this addition the temperature was maintained at 40° C. and the mixture, which gradually thickened, stirred continuously. Stirring was continued for 0.5 hr after the silica had been added. The mixture was charged to a 3-liter rocking autoclave which was agitated for 4 hours while the temperature was raised to 175° C. The autoclave was then left static at this temperature for 7 days. Thereafter the autoclave was opened and the white crystalline zeolite which had formed was separated from the mother liquor by decantation.

(b) Pre-treatment of zeolite

The crystalline zeolite was then washed thoroughly first with deionised water and then with a 10% nitric acid solution. Thereafter the acid treated zeolite was washed thoroughly with deionised water. to remove any traces of acid. This was then dried in a vacuum oven at 100° C. for 16 hours.

The dried zeolite was then calcined in an oven by raising the temperature to 500° C. over 4 hours and holding at that temperature for 60 hours.

The calcined zeolite was then refluxed in 1.6 l of 10% nitric acid for 2.5 hours and then water washed and dried in a cacuum oven as before.

The acid-washed zeolite was then subjected to ammonia exchange by refluxing in 1.5 l of 0.67 molar ammonium nitrate solution for 4 hours. It was then water-washed and dried as previously to give the ammonia exchanged zeolite.

The ammonia exchanged zeolite was recalcined by raising the temperature to 500° C. and maintained at that temperature for 16 hours to give the H-zeolite.

(c) Gallium-exchange

The H-zeolite from the recalcination step was placed in 1.65 l of a solution containing 0.065 moles of gallium nitrate and refluxed for 4 hours. The gallium exchanged material was then water-washed and dried in a vacuum oven as before.

(d) Incorporation of binder 200 g gallium exchanged zeolite were mixed with 213 g of Ludox AS 40 (Registered Trade Mark containing 40% $SiO_2$) and the resulting slurry was dried in a vacuum oven as previously described. The dried product was then broken and sieved to pass 12 to 30 mesh BSS.

EXAMPLES 2–4

A feedstock comprising a mixture of n-butane (77.4%), isobutane (12.8%), propane (8.8%), and but-2-ene (1.0%), percentages being by weight, was subjected to dehydrocyclodimerisation over 200 ml of the catalyst prepared as described in Example 1. The reaction conditions used and the results obtained are shown in the Table below.

TABLE

| | Example No. | | |
|---|---|---|---|
| | 2 | 3 | 4 |
| Time on stream (hours) | 1¼–2¼ | 4¼–5¼ | 3¼ |
| Average bed temp (°C.) | 535 | 535 | 535 |
| Pressure (bar) | 6 | 6 | 2 |
| LHSV | 2 | 2 | 6 |
| Contact time (sec) | 18 | 18 | 6 |
| Recovery (mass balance) | 95.6 | 102.4 | 100.2 |
| Products $H_2$ | 2.1 | 2.5 | 4.9 |
| $C_1$ | 26.0 | 26.7 | 22.4 |
| $C_2$ | 17.2 | 14.0 | 10.5 |
| $C_3+$ | 3.8 | 3.6 | 3.9 |
| $C_3-$ | 0.3 | 0.2 | 0.4 |
| $nC_4+$ | 1.2 | 0.3 | 0.4 |
| $iC_4+$ | 0.2 | — | 0.1 |
| $C_4-$ | — | — | — |
| $C_5-C_8$ | 1.5 | 1.1 | 0.4 |
| Benzene | 12.9 | 14.2 | 19.0 |
| Toluene | 14.8 | 16.7 | 19.1 |
| $C_8$ aromatics (e-benz) | 1.0 | 0.7 | 0.7 |
| $C_8$ aromatics (p-xyl) | 4.2 | 4.0 | 3.4 |
| $C_8$ aromatics (m-xyl) | 7.7 | 8.4 | 8.7 |
| $C_8$ aromatics (o-xyl) | 3.2 | 3.6 | 3.5 |
| $C_9$ aromatics | 3.5 | 3.6 | 3.0 |
| $>C_9$ aromatics | * | * | * |
| Coke | 0.4 | 0.4 | 0.1 |
| Total aromatics | 47.3 | 51.2 | 57.4 |

*Not determined

We claim:

1. An improved method of preparing a catalyst composition comprising a zeolite in which some or all of the cations have been exchanged for gallium ions, said zeolite having a high silica to alumina ratio and being prepared by crystallisation from an aqueous solution comprising a mixture of a source of silica, a source of alumina, and at least two other components selected from the group of alkali metal ions, ammonia and an organic nitrogen containing base, said improvement comprising washing the crystallised zeolite with acidified and/or deionised water, calcining the washed product at an elevated temperature, contacting the calcined product with an acid, refluxing the acid-treated product with a solution of a gallium compound to produce a gallium exchanged zeolite and washing the gallium exchanged zeolite with water to render it substantially free from any impregnated gallium or gallium compound.

2. A method according to claim 1 wherein the organic nitrogen-containing base is selected from a quaternary ammonium base, a pyrrolidine, an alkyldiamine containing from 2 to 20 carbon atoms and an alkanolamine.

3. A method according to claim 2 wherein the alkanolamine is selected from mono-ethanolamine, di-ethanolamine, mono-propanolamine and di-propanolamine.

4. A method according to claim 1 wherein the ratio of the silica source to the alumina source is in the range from 10:1 to 500:1 based on the equivalent moles of silica and alumina in the respective sources.

5. A method according to claim 1 wherein the alkali metal ion or ammonia source is present in an amount from 0.01 to 50 moles of alkali metal per mole equivalent of total silica and alumina in the respective sources.

6. A method according to claim 1 wherein the organic nitrogen-containing base is present in an amount from 0.02 to 50 moles per mole equivalent of total silica and alumina in their respective sources.

7. A method according to claim 1 wherein the acid used is a mineral acid selected from nitric, sulphuric, hydrochloric and hydrofluoric acid.

8. A process according to claim 1 wherein the crystallised zeolite is subjected to one or more treatments with ammonia before or after contact with the acid.

9. An improved method of preparing a catalyst composition according to claim 1 said improvement comprising washing the crystallised zeolite with acidified and/or deionised water, calcining the water washed product at a temperature between 300° and 800° C., contacting the calcined product with an acid, contacting the acid treated zeolite with ammonia or ammonium ions, recalcining the ammonia treated product at a temperature between 350° and 700° C., refluxing the recalcined product with a solution of a gallium compound to produce a gallium exchanged zeolite and washing the gallium exchanged zeolite with water to render it substantially free from any impregnated gallium or gallium compound.

10. A method according to claim 1 wherein the recalcined product is subjected to a gallium exchange by refluxing the calcined zeolite with a solution of gallium nitrate and washed with deionised water so that the gallium exchanged zeolite is substantially free from any impregnated gallium or gallium compound.

* * * * *